(12) United States Patent
Steiner

(10) Patent No.: US 6,508,830 B2
(45) Date of Patent: Jan. 21, 2003

(54) SUTURE ANCHOR

(75) Inventor: Anton J. Steiner, Wharton, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 57 days.

(21) Appl. No.: 09/844,076

(22) Filed: Apr. 30, 2001

(65) Prior Publication Data

US 2002/0161401 A1 Oct. 31, 2002

(51) Int. Cl.$^7$ ............................................... A61B 17/00
(52) U.S. Cl. ......................................... 606/232; 606/73
(58) Field of Search ................................. 606/232, 228, 606/230, 231, 72, 73, 104, 77, 78, 76

(56) References Cited

U.S. PATENT DOCUMENTS

| | | | |
|---|---|---|---|
| 5,522,843 A | * | 6/1996 | Zang ........................... 606/232 |
| 5,720,766 A | * | 2/1998 | Zang et al. .................. 606/232 |
| 5,733,307 A | * | 3/1998 | Dinsdale ...................... 606/232 |
| 5,814,070 A | * | 9/1998 | Borzone et al. ............. 606/232 |
| 5,824,011 A | | 10/1998 | Stone |
| 5,851,219 A | * | 12/1998 | Goble et al. ................. 606/232 |
| 5,899,920 A | * | 5/1999 | De Satnick et al. ........ 606/232 |
| 5,904,704 A | * | 5/1999 | Goble et al. ................. 606/232 |
| 5,941,882 A | | 8/1999 | Jammet et al. |
| 5,968,047 A | | 10/1999 | Reed |
| 6,096,060 A | * | 8/2000 | Fitts et al. ................... 606/232 |
| 6,111,164 A | | 8/2000 | Rainey et al. |
| 6,139,565 A | * | 10/2000 | Stone et al. ................. 606/232 |
| 6,168,598 B1 | * | 1/2001 | Martello ....................... 606/74 |
| 6,231,606 B1 | * | 5/2001 | Graf et al. .................... 623/13 |
| 6,264,677 B1 | * | 7/2001 | Simon et al. ................ 606/232 |
| 6,267,766 B1 | * | 7/2001 | Burkhart ....................... 606/72 |

* cited by examiner

Primary Examiner—Gloria M. Hale
(74) Attorney, Agent, or Firm—John S. Hale; Gipple & Hale

(57) ABSTRACT

A suture anchor comprising a cylindrical body portion with in inwardly tapered distal end portion has a screw thread extending along the cylindrical body portion and a plurality of parallel longitudinal grooves cut into the cylindrical body interrupting opposed portions of the screw thread. A suture cavity is transversely cut through the distal end portion and engages the plurality of longitudinal grooves, the suture cavity being dimensioned to hold at least one suture. The distal end portion defines a suture pathway comprising two separated leg members, each of which has an inner angled end surface leading into the suture cavity providing an entry passageway for a suture into the suture cavity and a driver for the suture anchor.

42 Claims, 3 Drawing Sheets

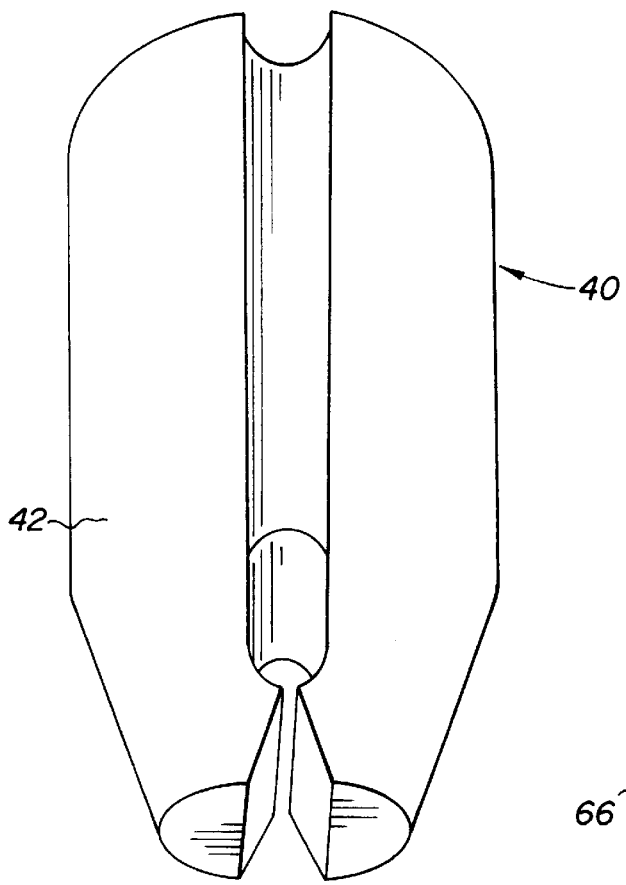
Fig. 4
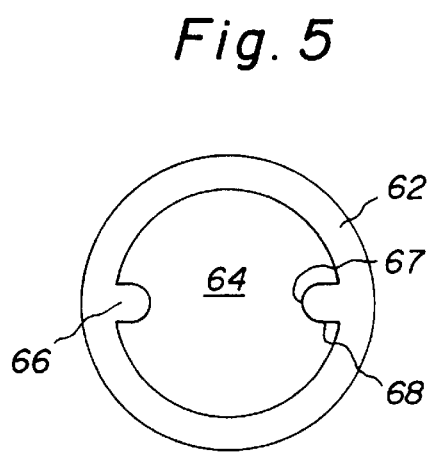
Fig. 5
Fig. 6
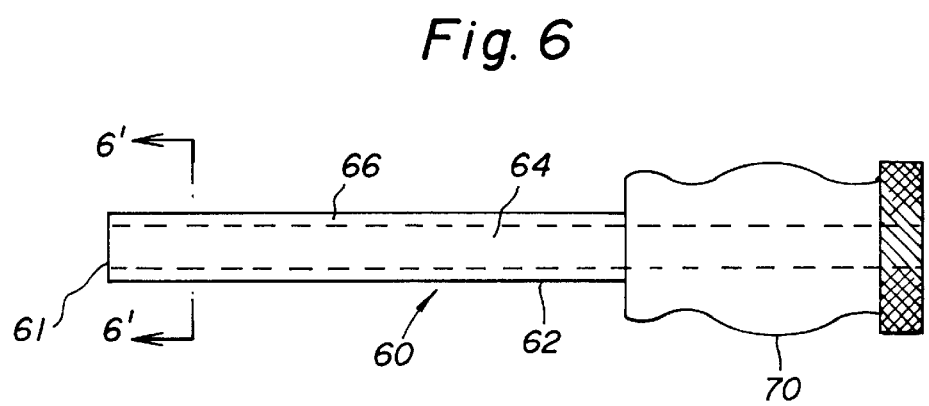

SUTURE ANCHOR

RELATED APPLICATIONS

There are no related applications.

BACKGROUND OF THE INVENTION

1. Field of Invention

The field of art to which this invention relates is generally directed to suture anchors and more specifically suture anchors constructed of allograft bone with a bottom clip assembly for receiving and holding the sutures.

2. Description of the Prior Art

As the treatment of injuries to joints and soft tissue has progressed, a need has developed for medical devices which can be used to attach tendons, ligaments and other soft tissue to bone. When surgically repairing an injured joint, it is preferable to restore the joint by reattaching the damaged soft tissues such as ligaments and tendons to bone rather than replacing them with an artificial material.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. There are well over 500,000 surgical procedures performed in the United States annually in which soft tissue was attached to a bone in various joints including the shoulder, hip and knee.

One conventional orthopedic procedure for reattaching soft tissue to bone is performed by initially drilling holes or tunnels at predetermined locations through a bone in the vicinity of a joint. The surgeon approximates soft tissue to the surface of the bone using sutures threaded through these holes or tunnels. This method is a time consuming procedure resulting in the generation of numerous bone tunnels. The bone tunnels, which are open to various body fluids and infectious agents, may become infected or break and complications such as longer bone-healing period may result. A known complication of drilling tunnels across bone is that nerves and other soft tissue structures may be injured by the drill bit or orthopaedic pin as it exits the far side of the bone. Also, it may be anatomically impossible or at least very difficult to reach and/or secure a suture that has been passed through a tunnel. When securing the suture or wire on the far side of the bone, nerves and soft tissues can become entrapped and damaged.

Screws are also used to secure soft tissues adjacent to the bone surface. Screws suffer from the disadvantage that they tend to loosen with time, thereby requiring a second operation to remove the loosened screw. In addition, when the screws are set in bone, the heads of the screws frequently protrude above the surface of the bone in which they are set, thereby presenting an abrasive surface which may create wear problems with surrounding tissue. Once a hole has been made in the bone it may be impossible to relocate the hole in a small distance away from its original position due to the disruption of the bone structure created by the initial hole. Finally, the nature of a screw attachment tends to require a flat attachment geometry; the pilot hole must generally be located on a relatively flat section of the bone, and toothed washers must frequently be used in conjunction with the screws to fasten the desired objects to the target bone. As a result of these constraints, it may be necessary to locate the attachment point at less than an optimal position.

Staples are also used to secure soft tissue adjacent the bone surface. Staples suffer from their own set of disadvantages and generally must frequently be removed after they have been in position for some time, thereby necessitating a second operation In addition, staples must generally be positioned so as to maximize their holding power in the bone which may conflict with the otherwise-optimal position for attachment of the objects to bone. Staples have also been known to crack the bone during deployment, or to accidentally transect the object (e.g. soft tissue) being attached to the bone, since it tends to be difficult to precisely control the extent of the staple's penetration into the bone. Additionally once the staple has been set into the bone the position of the staple is then effectively determined, thereby making it impossible to thereafter adjust the position of the staple or to adjust the degree of tension being applied to the object which is being attached to the bone without setting a new staple.

In order to overcome a number of the problems associated with the use of the conventional soft tissue to bone attachment procedures, suture anchors have been developed and are now frequently used to attach soft tissue to bone. A suture anchor, commonly referred to as a bone anchors, is an orthopedic, medical device which is typically implanted into a cavity drilled into a bone. In the present application, the device will be referred to as a suture anchor. The bone cavity is typically referred to as a bore hole and if it does not extend through the bone is typically referred to as a "blind hole". The bore hole is typically drilled through the outer cortical layer of the bone and into the inner cancerous layer. The suture anchor may be engaged in the bore hole by a variety of mechanisms including friction fit, barbs which are forced into the cancellous layer of bone or by threading into pre-threaded bores in the bone mass or using self tapping threads. Suture anchors have many advantages including reduced bone trauma, simplified application procedures, and decreased likelihood of suture failure. Suture anchors may be used in shoulder reconstruction for repairing the glenohumeral ligament and may also be used in surgical procedures involving rotator cuff repair, ankle and wrist repair, bladder neck suspension, and hip replacement.

Suture anchors typically have a hole or opening for receiving a suture. The suture extends out from the bore hole and is used to attach soft tissue. The suture anchors presently described in the art may be made of absorbable materials which absorb over time, or they may be made from various non-absorbable, biocompatible materials. Although most suture anchors described in the art are made from non-absorbable materials, the use of absorbable suture anchors may result in fewer complications since the suture anchor is absorbed and replaced by bone over time. The use of absorbable suture anchors may reduce the likelihood of damage to local joints caused by anchor migration. Moreover, when an absorbable suture anchor is fully absorbed it will no longer be present as a foreign body. It is also advantageous to construct the bone anchor out of allograft cortical bone as this material will result in natural filling in of the bore with bone in the original bone base and the elimination of foreign material from the site.

It is also a problem that most of the bone anchors currently used are prepacked with sutures attached in kit form forcing the surgeon to use a specific type of suture and the hospital to carry large numbers of bone anchors in inventory with varying suture sizes.

A number or prior art patents such as U.S. Pat. Nos. 5,941,882 and 5,733,307 are directed toward threaded bone screws and bone anchors which have grooves or troughs cut longitudinally along the anchor body intersecting the threads to receive sutures during the bone anchor insertion process.

U.S. Pat. No. 5,824,011 is directed toward threaded bone inserts which have channels cut into their bodies to receive driver torque applicators.

U.S. Pat. No. 6,111,164 shows a bone insert which is formed from human cortical bone which are adapted to be driven into bone and U.S. Pat. Nos. 5,858,749 and 5,968,047 disclose bone fixation devices such as bone screws, anchors and the like fabricated from bone tissue.

Although suture anchors for attaching soft tissue to bone are available for use by the orthopedic surgeon, there is a need in this art for novel suture anchors having improved performance characteristics, such as ease of insertion and greater resistance to "pull-out".

SUMMARY OF THE INVENTION

The present invention is directed toward a suture anchor constructed of animal bone preferably cortical human bone which is threaded and has a plurality of longitudinal grooves cut into its outer surface intersecting the helical thread to hold suture strands and the drive elements of a driver instrument. The lower distal end is tapered and formed with two separated leg portions, each of which has an inclined inner surface leading to a suture cavity cut in the suture anchor body transverse to the longitudinal axis of the bone anchor body.

The present invention provides a technical advantage in that it provides a channel in the suture anchor in which the suture resides during insertion of the bone anchor into the bone while also allowing the driver to be in the form of a drive socket rather than an end torque applying device to provide a bone anchor that is less susceptible to mechanical breakage.

It is thus an object of the present invention to provide a suture anchor which can be used with a wide variety of sutures from different manufacturers allowing the surgeon the choice of sutures and suture composition, thus saving the hospital from stocking a large number of prepacked bone anchors and suture kits.

Therefore, it is another object of the present invention to provide a suture anchor which is simple to apply and is mechanically stable when implanted in bone.

It is a further object of the present invention to provide an absorbable suture anchor made of cortical bone.

Accordingly, one of the objects of the present invention is to provide an allograft suture anchor which promotes the use of natural bone growth in the bone bore.

Another object of the present invention is to provide a novel suture anchor for anchoring one end of a piece of conventional suture in bone by simply snapping the suture length through an open end into the suture chamber leaving the suture residing free outside the bone so that the free end of the suture can then be used to attach the desired object (e.g. a ligament or prosthesis) to the bone.

Yet another object of the present invention is to provide a novel suture anchor for anchoring one end of a piece of conventional suture in bone which anchor will attach itself securely to the target bone and which has virtually no tendency to migrate from its deployment site.

And another object of the present invention is to provide a novel suture anchor for anchoring one end of a piece of conventional suture in bone which has high tissue acceptability, prevents back out and is reliable in use.

These and other objects, advantages, and novel features of the present invention will become apparent when considered with the teachings contained in the detailed disclosure along with the accompanying drawings.

BRIEF DESCRIPTION OF THE DRAWINGS

FIG. 4 is a perspective view of another embodiment of the bone suture anchor;

FIG. 5 is a perspective view of the driver for the bone suture anchor of FIG. 1 and FIG. 4;

FIG. 6 is an enlarged cross sectional view of the driver of FIG. 5 taken along line 6'—6' with anchor mounted therein.

DETAILED DESCRIPTION OF THE PREFERRED EMBODIMENT

Figure 1:
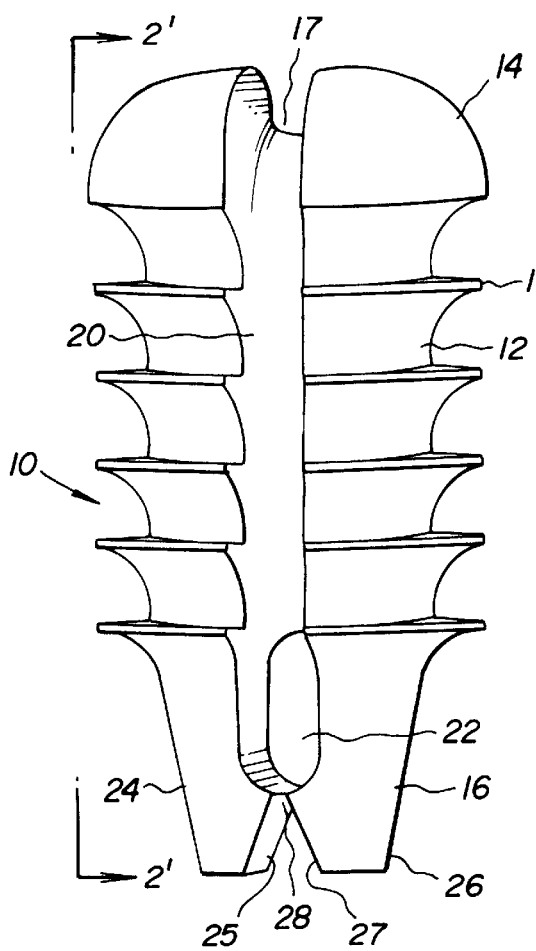
FIG. 1 is a perspective view of the inventive bone suture anchor.
Figure 2:
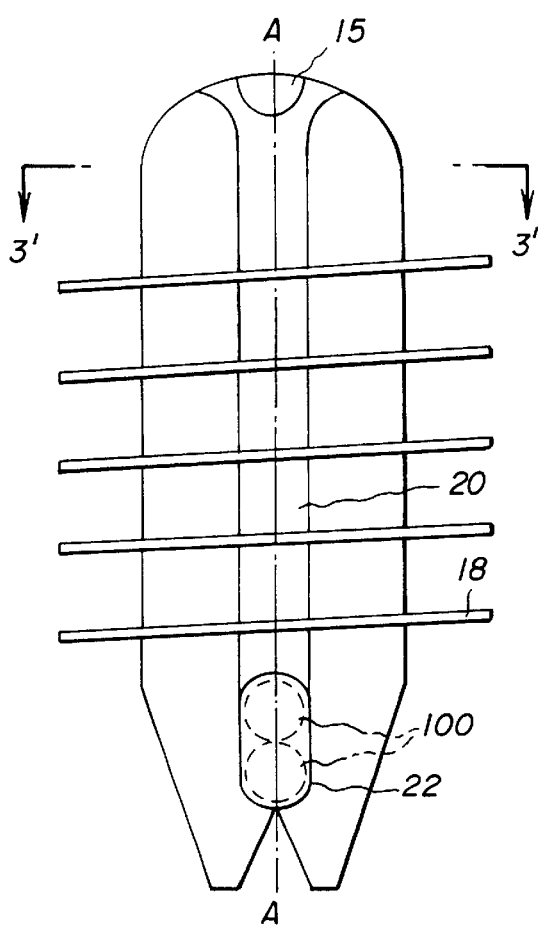
FIG. 2 is a cross sectional view of the bone suture anchor of FIG. 1 taken along line 2'—2' with mounted sutures shown in phantom.

The preferred embodiment and the best mode of the invention as shown in FIGS. 1 and 2 is a bone or suture anchor 10 with a cylindrical body 12 having a rounded proximal head 14 and a tapered split distal end 16 which is initially inserted into the bore in the bone mass 200. The split distal end 16 tapers inward in a range from 10° to 20° and preferably 15° from the center longitudinal axis of the suture anchor for self centering insertion and has a smooth truncated outer surface. Preferably, the bone anchor is manufactured from cortical human bone and may be partially demineralized and alternately treated with bone morphogenic protein, hylauronic acid and a phosphate buffer for quicker bone formation once the suture anchor has been threaded into the bone. Alternately, the suture anchor may be manufactured from a biocompatible and bioresorbable material such as xenograft bone, plastic or a biocompatible metal such as titanium or stainless steel.

The rounded head 14 is dome shaped for minimum soft tissue impingement and can alternatively be provided with a recessed drive pocket 15 which serves to center the driver socket. If desired, the drive pocket 15 as shown in phantom in FIG. 2 can also be shaped so that it also aids in driving the bone anchor 10. A driver positioning groove 17 is cut into the surface of the rounded dome leading into suture/driver grooves 20 allowing the driver 60 to be easily and properly seated on the suture anchor 10 to deliver driving torque to same. The depth of groove 20 is such that the suture 100 is seated below the dome surface and beneath the driver 60. The diameter of the suture anchor 10 preferably runs between 4.0 mm and 6.0 mm based upon the final thread pitch and depth of thread and the length of the suture anchor ranges from 8.0 mm to 12.0 mm with a preferred length of 10 m Threads 18 are cut in the body 10 in a helical pattern or in a parallel pattern depending upon the insertion used and suture/driver channels or grooves 20 are longitudinally cut parallel to each other on the sides of the screw body intersecting threads 18. The threads are standard machine thread with maximum thread depth and pitch and are well known in the art and any number of standard machine threads of appropriate size and thread configuration can be used. The channels or grooves 20 are preferably located on opposing sides of the body 10 and have a width greater than or equal to the diameter of the suture and a depth which is preferably at least twice the diameter of the suture 100 extending into the anchor body past the minor or base diameter of the thread 18. The suture 100 is preferably a #2 suture, a standard suture made of absorbable, synthetic absorbable or non-absorbable material ranging in length from 5 to 60 inches. The grooves 20 each have a bottom radius to minimize stress concentration of groove corners and will allow two sutures 100 to lay below the minor thread diameter. The grooves 20 lead to an oval or oblong shaped through going suture holding cavity 22 cut transversely through the distal end of the body 10 and extend longitudinally parallel to the axis of the screw body into the rounded head 14. The drive/holding grooves 20 are constructed so that the sutures will track in the channels and through the cannulation 64 in the driver inserter body 62. The grooves 20 also function as drive slots and are used to insert the suture anchor 10 to the same level on the resident bone mass each and every time. The driver and insertion instrument 60 will back off the suture anchor 10 as the instrument tip contacts the adjoining bone tissue 200. The tapered rounded exterior surfaced distal end 16 of the suture anchor is formed with a split tip forming two leg sections 24 and 26, each of which have inwardly angled planar cut end surfaces 25 and 27 forming a "V" configuration. The "V" forms an angle running from 20° to 45° preferably 30° with the bottom of the "V" being opened at 28 to form an entrance pathway into the suture cavity 22. The leg sections or members 24 and 26 have a slight spring or flexibility of about 1° to 2° from the center longitudinal axis allowing them to be slightly spread apart against the force of the suture 100 and in combination with the suture compression accommodate suture entry. The distal tip feature of the bone anchor allows easy suture loading and provides significant advantages over other threaded designs. The split tip offers easy loading of the suture 100 into the suture cavity 22, which is wide enough 0.1 mm–0.5 mm to accommodate two #2 sutures or more as is desired. While the preferred embodiment shows the chamber 22 as oval shaped, it can be round or of another configuration as desire to accommodate one or more sutures. The location of the suture cavity toward the distal end of the suture anchor eliminates pullout problems which occur when the suture cavity is positioned in the proximal end of the suture anchor. The distal tip is tapered to facilitate easier guidance of the suture anchor into the bone mass area 200, with the top of the cavity 22 preferably being located below the major diameter of the anchor. The cavity positioning assures that the slotted cross section will not receive torsional loading from insertion. The suture cavity 22 is preferably oval or oblong in configuration and sized to hold two separate sutures 100.

An alternate embodiment 40 of the suture anchor is shown in FIG. 4 and has the same configuration and structure as suture anchor 10 with the exception that the exterior surface 42 is smooth and not threaded.

Figure 3:
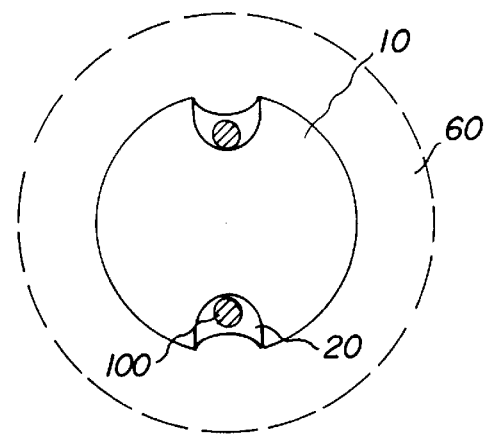
FIG. 3 is a cross sectional view of the bone section of FIG. 1 taken along lines 3'—3' with sutures sutures and drive members shown in phantom.
Figure 7:
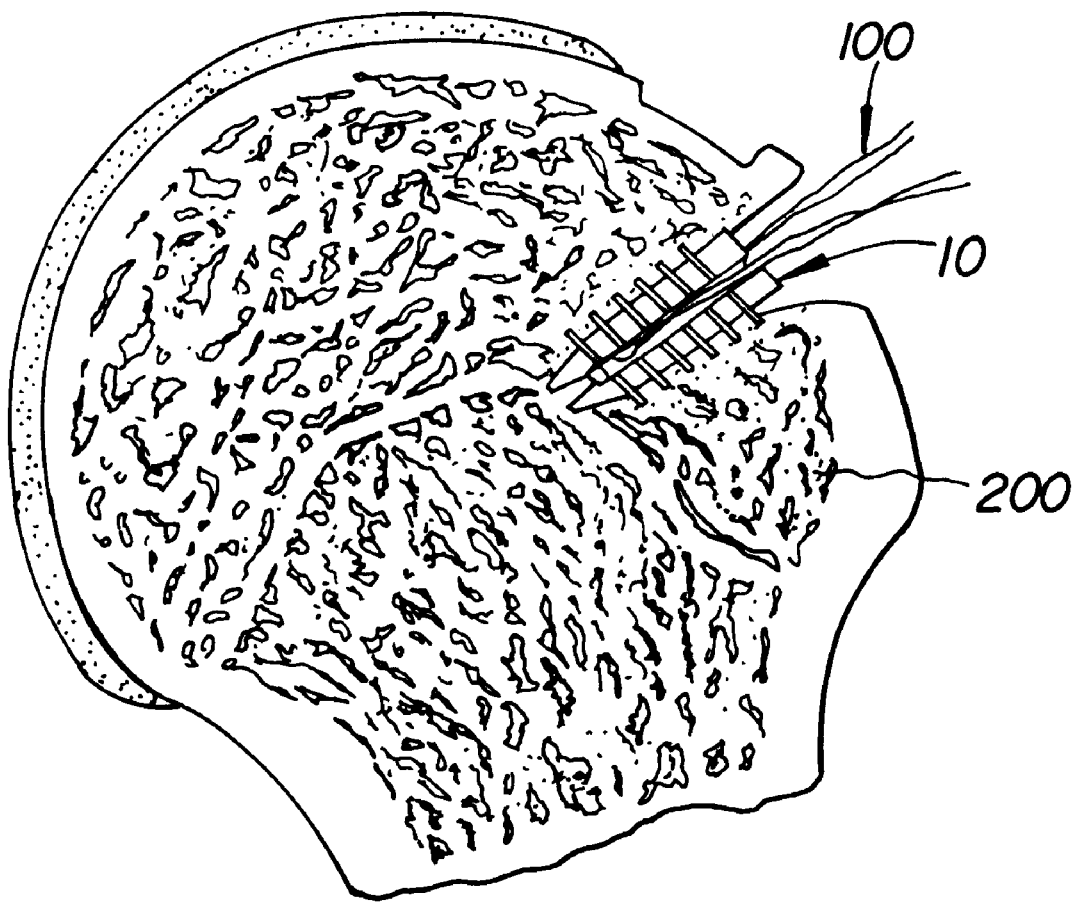
FIG. 7 is a cross sectional view of the bone suture anchor of FIG. 1 mounted in the humeral rim bone with the suture attached.

The suture anchor 10 is adapted for insertion into the distal end 61 of a driver 60 as shown in FIGS. 3 and 5. The driver 60 is provided with drive ribs 66 which extend into the interior cannula 64 of the cylindrical driver body 62. The drive ribs 66 preferably have a rounded end surface 67 so that they do not cut the suture located beneath them and have a width equal to or slightly less than the width of the grooves 20 so that when the drive ribs 66 are inserted into the grooves or channels 20 overlapping the seated sutures 100 driving torque can be applied to the suture anchor 10 groove walls via twisting of the driver handle 70. The side walls 68 of the drive ribs 66 engage the side walls of the suture anchor groove 20 to drive the suture anchor 10 into a threaded or smooth bore hole previously cut in the bone mass 200. The suture anchor drive geometry is unique in that the suture(s) 100 and driver rib 66 use the same anchor groove 20. The sutures 100 will track in the cavity 22, grooves 20 and through the cannulation 64 of the driver/inserter 60.

In operation the suture 100 is loaded into the cavity 22 of the suture anchor 10 by pulling the same taut through the split legs 24 and 26 slightly springing the same and compressing the suture until the suture enters into cavity 22. Once the suture 100 is housed in the cavity 22 the suture 100 is pulled taut up the suture anchor 10 along channel or grooves 20. The suture anchor 10 is then mounted in the driver 60 with the suture 100 pulled through the driver cannula 64 and drive nibs 66 mounted in the grooves 20 over the top of the sutures 100. As the suture anchor is screwed into the bone 200 the bone surrounds the grooves 20 to hold the suture 100 within the groove 20. The suture anchor 10 is then seated in the bore previously drilled into the bone with the driver 60 having been backed off during the torque application. The surgeon can then attach the suture opposite the suture anchor 10 to the soft tissue and pull the soft tissue to the bone 200. Because the suture is a single piece of material the failure strength is the suture line break strength rather than the pull out strength where two separate pieces of suture are used. Pull out of the anchor is also diminished because of the deeper seating of the suture in the bone anchor and encompassing bone mass.

In the foregoing description, the invention has been described with reference to a particular preferred embodiment, although it is to be understood that specific details as shown are merely illustrative, and the invention may be carried out in other ways without departing from the true spirit and scope of the following claims.

What I claim are:

1. A sterile suture anchor comprising:
   a cylindrical body portion with a generally tapered distal end portion,
   a screw thread extending along said cylindrical body portion,
   a plurality of longitudinal grooves cut into said cylindrical body interrupting opposed portions of said screw thread;
   a suture cavity transversely cut through said distal end portion engaging said plurality of longitudinal grooves, said suture cavity being dimensioned to hold at least one suture; and
   a suture pathway means formed in said distal end portion communicating with said suture cavity allowing a suture to be inserted via said suture pathway means into said cavity.

2. A sterile suture anchor according to claim 1 wherein said suture pathway means comprises a V shaped recess leading into said cavity.

3. A sterile suture anchor according to claim 1 wherein said suture pathway means comprises two separated legs, each of which has an inner angled surface leading into said cavity.

4. A sterile suture anchor according to claim 1 wherein said suture pathway means comprises two separate leg members, each leg member comprising a rounded tapered outer surface and an inwardly angled end surface directed toward said cavity and providing an entry passageway for a suture into said cavity.

5. A sterile suture anchor according to claim 4 wherein said leg members are slightly flexible from about 1° to about 2° to the extent that a suture can be pulled past the leg members into said cavity.

6. A sterile suture anchor according to claim 2 wherein said head portion of said suture anchor is round and has a groove cut therein which interconnects with at least two of said longitudinal grooves.

7. A sterile suture anchor according to claim 1 wherein said longitudinal grooves are adapted to receive a portion of said length of suture so as to: (i) recess said suture within said suture cavity and seat said suture so that said suture will not interfere with the receipt of a torque applying portion of a suture anchor driver, and (ii) allow for sliding movement of said suture relative to said said suture anchor body once said suture anchor has been inserted in a bone mass.

8. A sterile suture anchor as claimed in claim 1 wherein said suture anchor is constructed of allograft bone.

9. A sterile suture anchor as claimed in claim 1 wherein said suture anchor is constructed of xenograft bone.

10. A sterile suture anchor as claimed in claim 1 wherein said suture anchor is constructed of plastic.

11. A sterile suture anchor as claimed in claim 1 wherein said suture anchor is constructed of metal.

12. A sterile suture anchor as claimed in claim 11 wherein said suture anchor metal is titanium.

13. A sterile suture anchor as claimed in claim 11 wherein said suture anchor metal is stainless steel.

14. A sterile suture anchor as claimed in claim 8 wherein said allograft bone is cortical human bone.

15. A sterile suture anchor according to claim 1 wherein said suture body has a head portion which is dome shaped.

16. A sterile suture anchor according to claim 1 wherein said distal portion is split into separated sections defining an angled pathway leading into said suture cavity.

17. A sterile suture anchor according to claim 1 wherein said distal portion has a smooth rounded outer surface.

18. A sterile suture anchor according to claim 2 wherein said suture pathway means defines a V shaped recess which opens into said cavity with the narrower portion of said cavity opening being slightly smaller than the diameter of the suture being used.

19. A sterile biocompatible absorbable suture anchor comprising:
a cylindrical body portion with a generally tapered distal end portion,
a screw thread extending along said cylindrical body portion,
a plurality of parallel longitudinal grooves cut into said cylindrical body interrupting opposed portions of said screw thread;
a suture cavity transversely cut through said distal end portion engaging said plurality of longitudinal grooves, said suture cavity being dimensioned to hold at least one suture; and
a suture pathway means formed in said distal end portion communicating with said suture cavity allowing a suture to be inserted into said cavity, said suture pathway means comprising two separated legs, each of which has an inner angled surface leading into said cavity and providing an entry passageway for a suture into said cavity.

20. A suture anchor as claimed in claim 19 wherein said suture grooves are cut into the body of said suture anchor to completely contain a suture mounted in said suture anchor such that said bone anchor may be inserted into said bone without frictional contact between said bone and said suture.

21. A sterile suture anchor as claimed in claim 19 wherein said suture anchor is constructed of allograft bone.

22. A sterile suture anchor as claimed in claim 19 wherein said suture anchor body is constructed of human cortical bone.

23. A sterile suture anchor according to claim 19 wherein said suture body has a head portion which is dome shaped with a groove cut in said dome shaped head portion leading into at least two of said longitudinal groove.

24. A sterile suture anchor according to claim 19 wherein said separated legs form a composite inner surface angle leading into said cavity from about 20° to about 45°.

25. A sterile suture anchor according to claim 24 wherein said separated legs have a smooth rounded outer surface.

26. A sterile suture anchor according to claim 19 wherein said suture cavity is oval and can hold at least two sutures.

27. A sterile suture anchor according to claim 19 wherein said suture cavity is oblong and can hold at least one suture.

28. A sterile suture anchor for insertion into bone comprising:
an anchor body constructed of cortical bone, said bone anchor body having a driver end and a lead-in end, said bone anchor body having a threaded surface formed by broken threads with said threaded surface having a plurality of suture grooves extending longitudinally along said anchor body and cut into said bone anchor body at a depth to hold a suture;
said suture grooves extending into a suture cavity formed transverse to a longitudinal axis of the bone anchor body and extending through said bone anchor body, and a suture loading slot extending from said lead-in end into said suture cavity.

29. A sterile suture anchor as claimed in claim 28 wherein said suture anchor slot is substantially V shaped.

30. A sterile suture anchor as claimed in claim 28 wherein said suture anchor slot is formed by two opposing separated members which forms said suture loading slot.

31. A sterile suture anchor according to claim 28 wherein said suture body has a head portion which is dome shaped with a groove cut therein which engages said longitudinal suture grooves.

32. A sterile suture anchor according to claim 28 wherein said lead-in end is tapered inward from about 10° to about 20° from the longitudinal axis of the suture anchor and is split into separated sections defining an angled pathway leading into said suture cavity.

33. A sterile suture anchor according to claim 32 wherein said lead-in end separated sections have a smooth rounded outer surface.

34. A sterile suture anchor comprising:
a cylindrical body portion with a generally tapered distal end portion,
said cylindrical body portion and generally tapered distal end portion being provided with a substantially smooth outer surface,
a plurality of parallel longitudinal grooves cut into said cylindrical body a depth greater than the diameter of the suture used in the suture anchor;
a suture cavity transversely cut through said distal end portion engaging said plurality of longitudinal grooves, said suture cavity being dimensioned to hold at least one suture; and
a suture pathway means formed in said distal end portion communicating with said suture cavity allowing a suture to be inserted into said cavity, said suture pathway means comprising a distal portion split into separated sections defining a pathway leading into said suture cavity.

35. A sterile suture anchor as claimed in claim 34 wherein said suture anchor is constructed of bone.

36. A sterile suture anchor as claimed in claim 34 wherein said suture anchor body is constructed of human cortical bone.

37. A sterile suture anchor according to claim 34 wherein said suture body has a head portion which is dome shaped.

38. A sterile suture anchor according to claim 34 wherein said suture pathway means comprises two separated leg members, each of which has an inner angled end surface providing an entry passageway for a suture into said cavity.

39. A sterile suture anchor according to claim 34 wherein said distal portion has a smooth rounded outer surface.

40. A sterile suture anchor according to claim 34 wherein said distal portion leg sections are moveable when engaged by a suture from about 1° to about 2°.

41. A sterile suture anchor according to claim 34 wherein said suture anchor body ranges from about 4.0 mm to about 6.0 mm in diameter and 8.0 mm to 12.0 mm in length.

42. A sterile suture anchor and drive kit comprising:
- a suture anchor with a cylindrical body portion with a generally tapered distal end portion,
- a screw thread extending along said cylindrical body portion,
- a plurality of parallel longitudinal grooves cut into said cylindrical body interrupting opposed portions of said screw thread;
- a suture cavity transversely cut through said distal end portion engaging said plurality of longitudinal grooves, said suture cavity being dimensioned to hold at least one suture; and
- a suture pathway means formed in said distal end portion communicating with said suture cavity allowing a suture to be inserted into said cavity, said suture pathway means comprising two separated legs, each of which has an inner angled surface leading into said cavity and providing an entry passageway for a suture into said cavity;
- a driver adapted to be mounted to said suture anchor, said driver comprising a hollow tube with inwardly projecting drive ribs adapted to be inserted into said suture anchor longitudinal grooves and engage groove side walls of said suture anchor at a distance less than one half the depth of the groove to apply driving torque to said suture anchor.

* * * * *